United States Patent [19]

Kawasaki et al.

[11] Patent Number: 5,379,771
[45] Date of Patent: Jan. 10, 1995

[54] ULTRASONIC IMAGING APPARATUS

[75] Inventors: Shuichi Kawasaki; Masahiko Yano, both of Tochigi; Jiro Higuchi, Ootawara, all of Japan

[73] Assignee: Kabushiki Kaisha Toshiba, Kawasaki, Japan

[21] Appl. No.: 219,718

[22] Filed: Mar. 29, 1994

[30] Foreign Application Priority Data

Apr. 6, 1993 [JP] Japan .................................. 5-079822

[51] Int. Cl.$^6$ .............................................. A61B 8/00
[52] U.S. Cl. .............................. 128/661.1; 128/661.01; 128/661.09
[58] Field of Search ....................... 128/661.01, 661.07, 128/661.08, 661.09, 661.10, 662.01

[56] References Cited

U.S. PATENT DOCUMENTS

| | | | |
|---|---|---|---|
| 5,078,146 | 1/1992 | Sato . | |
| 5,156,152 | 10/1992 | Yamazaki et al. | 128/661.08 |
| 5,159,931 | 11/1992 | Pini | 128/660.07 |
| 5,197,477 | 3/1993 | Peterson et al. | 128/661.08 |

*Primary Examiner*—George Manuel
*Attorney, Agent, or Firm*—Finnegan, Henderson, Farabow, Garrett & Dunner

[57] ABSTRACT

An ultrasonic imaging apparatus comprised of an ultrasonic transducer array that transmits ultrasonic waves to a subject under examination and receives ultrasonic waves reflected from within the subject under examination and a scan controller that controls the transducer array to transmit/receive the ultrasonic waves in the same direction repeatedly and to change the transmitting/receiving direction of the ultrasonic waves in a sectional plane of the subject under examination. The apparatus also includes a detector that detects Doppler shifted frequency data at a plurality of points in the sectional plane from a received signal by the transducer array and a display that displays blood flow of the subject. A memory stores a plurality of types of patterns having a maximum velocity, a minimum velocity and a number of frames per unit time of blood flow to be detected in various combinations. A selector selects a pattern from the types of patterns, and a controller sets a parameter for the number of times the ultrasonic waves are repeatedly transmitted/received, a parameter for a repetition period during which the ultrasonic waves are repeatedly transmitted/received, and a parameter for the number of times the direction of transmission/reception of the ultrasonic waves is changed in the scanning plane. The controller also controls the scan controller and the detector in accordance with the set parameters so as to implement the pattern selected by the selector.

17 Claims, 8 Drawing Sheets

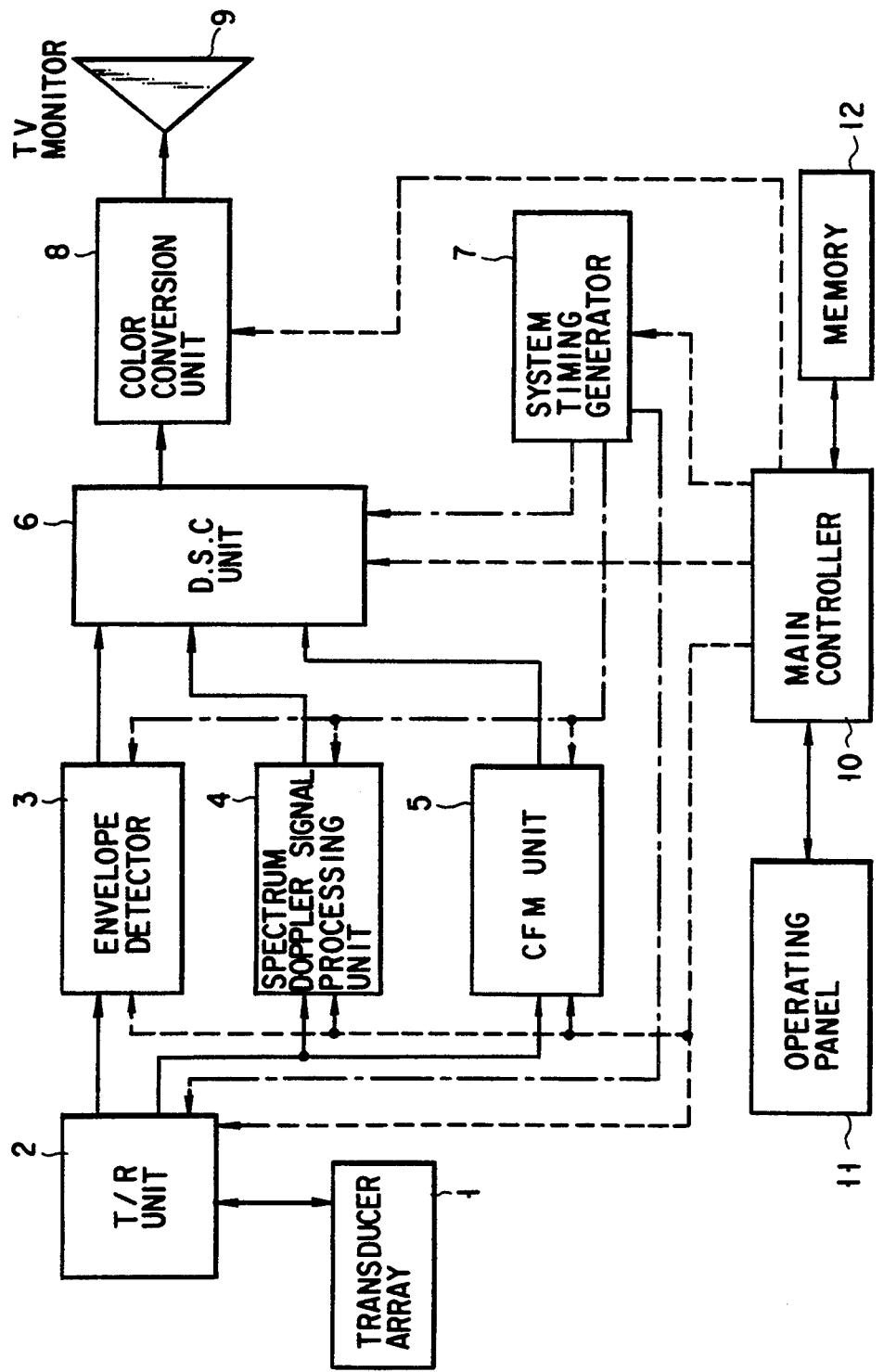
F I G. 1

ULTRASONIC IMAGING APPARATUS

BACKGROUND OF THE INVENTION

1. Field of the Invention

The present invention relates to an ultrasonic imaging apparatus which detects blood flow data at points in a two-dimensional scanning plane utilizing the Doppler effect and displays a color blood flow mapping image.

2. Description of the Related Art

Let transmitted frequency=f0, received frequency=f1, Doppler-shifted frequency=fd, blood flow velocity=v, sound velocity in living tissues=C, and angle between a beam of ultrasound and a blood vessel=$\theta$. Then the received frequency is represented by the equation $$f1 = \{(1 + V \cdot \cos\theta/C)/(1 - V \cdot \cos\theta/C)\} \cdot f0 \quad (1)$$
$$= (1 + 2V \cdot \cos\theta/C) \cdot f0$$

The Doppler-shifted frequency is represented by the equation $$fd = f1 - f0 = (2V \cdot \cos\theta/C) \cdot f0 \quad (2)$$

Using equations (1) and (2) the blood flow velocity is calculated from the Doppler-shifted frequency fd and the angle $\theta$.

Such a type of ultrasonic imaging apparatus needs the following parameters:

- N = the number of transmitting/receiving operations for the same raster (hereinafter referred to as the number of pieces of data);
- fr = rate frequency;
- P = low-flow-velocity detectability improvement ratio (also called the number of alternate stages), i.e., the number of other rasters on which ultrasound transmitting/receiving operations are performed between the moment that an ultrasound transmitting/receiving operation was performed on a certain raster and the moment that another ultrasound transmitting/receiving operation is performed on the same raster;
- fc = cutoff frequency of an MTI filter;
- MA = Moving Average;
- MAE = Motion Artifact eliminator;
- W = angle of field of view;
- Lp = raster pitch;
- Ln = the number of rasters With conventional ultrasonic imaging apparatus, an operator is required to adjust these parameters individually, which is troublesome and time-consuming. The adjusted values of those parameters are related with one another, so that the detectable velocity range (the detectable maximum velocity Vmax and minimum velocity Vmin) the operator wants to know truly and the number of frames per second (f/s) will vary. Thus, the operator is required to accumulate the meaning and the interrelation of the parameters as preliminary knowledge. The detectable velocity range and the number of frames per second must be changed according to an imaging region such as abdomen, lower leg, or the like.

For example, the detectable minimum velocity Vmin and maximum velocity Vmax are related to the rate frequency fr, the number of pieces of data N and the number of alternate stages P by the equations $$Vmin = \alpha \times ((C \times fr)/(2 \times N \times P \times F0 \times \cos\theta)) \quad (3)$$

$$Vmax = \alpha \times ((C \times fr)/(4 \times P \times f0 \times \cos\theta)) \quad (4)$$

where $\alpha$ is a constant.

Moreover, the number of frames per second f/s is related to the rate frequency fr, the number of pieces of data N and the number of rasters Ln by the equation $$f/s = \beta \times (Ln \times N)/fr) \quad (5)$$

where $\beta$ is a constant.

Furthermore, the number of rasters Ln is related to the angle of field of view w and the raster pitch P by the equation $$Ln = \gamma \times (W/LP) \quad (6)$$

where $\gamma$ is a constant.

SUMMARY OF THE INVENTION

It is therefore an object of the present invention to provide an ultrasonic imaging apparatus which permits a plurality of parameters required to make measurement of blood flow velocity utilizing the Doppler effect to be set readily.

According to the present invention there is provided an ultrasonic imaging apparatus comprising: an ultrasonic transducer array for transmitting ultrasonic waves to a subject under examination and receiving ultrasonic waves reflected from within said subject under examination; scan control means for controlling said transducer array so as to transmit/receive said ultrasonic waves in the same direction repeatedly and change the transmitting/receiving direction of said ultrasonic waves in a sectional plane of said subject under examination; detecting means for detecting Doppler shifted frequency data at a plurality of points in said sectional plane from a received signal by said transducer array; displaying means responsive to said Doppler shifted frequency data for displaying blood flow in said sectional plane in color; storage means for storing a plurality of types of patterns having the maximum velocity, the minimum velocity and the number of frames per unit time of blood flow to be detected by said detecting means in various combinations; selecting means for selecting a pattern out of said plurality of types of patterns manually; and control means for setting a parameter for the number of times said ultrasonic waves are transmitted/received repeatedly in the same direction, a parameter for a repetition period at which said ultrasonic waves are transmitted/received repeatedly, and a parameter for the number of times the direction of transmission/reception of said ultrasonic waves is changed in said scanning plane and controlling said scan control means and said detecting means in accordance with said parameters thus set so as to implement said pattern selected by said selecting means.

According to the present invention, there are held various patterns of the maximum velocity and the minimum velocity of blood flow and the number of frames per unit time. The values of parameters are set in the control means which are required by the apparatus (the transmitter/receiver means, the detecting means) to implement a pattern of patterns selected manually.

Therefore, an operator simply selects a pattern of the patterns manually, which relieves the operator of the burden of setting parameters required by the apparatus individually. In addition, the operator is relieved of the burden of correcting parameters which have been set to values impossible to implement, over and over again.

Each of the patterns comprises the maximum velocity and the minimum velocity of blood flow and the number of frames per unit time that the operator wants to know truly. The operator is therefore allowed to select a desired pattern out of patterns readily.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 is a block diagram of an ultrasonic imaging apparatus according to an embodiment of the present invention;

DETAILED DESCRIPTION OF THE PREFERRED EMBODIMENT

Figure 2:
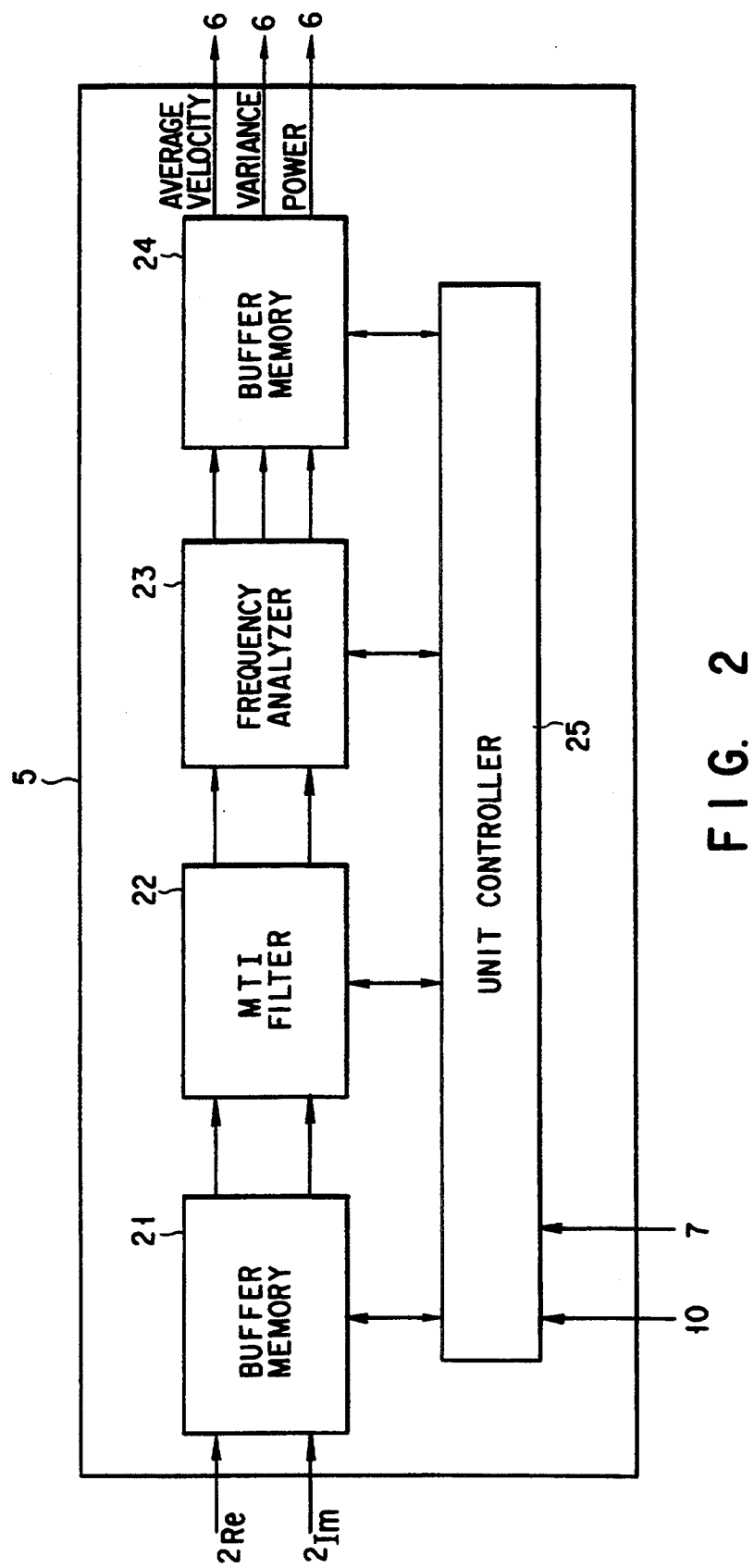
FIG. 2 is a block diagram of the color flow mapping unit (CFM) of FIG. 1.

Hereinafter, an embodiment of the present invention will be described in conjunction with the accompanying drawings.

Referring now to FIG. 1 there is shown an ultrasonic imaging apparatus embodying the present invention, in which solid lines indicate the flow of data signals, broken lines indicate the flow of control signals, and dash-and-dotted lines indicate the flow of timing signals.

An ultrasonic transducer array or probe 1 is an ultrasound transmitting/receiving means which is equipped with a large number of piezoelectric transducer elements arranged linearly. These transducer elements emit (transmit) ultrasonic waves to a subject under examination and receive reflected waves from tissues within the subject. A transmitter/receiver controller (T/R unit) 2 controls the transducer array 1. Thereby, ultrasonic waves emitted from transducer elements are focused into a beam of ultrasound, which, in turn, is subjected to oscillating movement (sector scan) or parallel translation (linear scan). A path taken by a beam of ultrasound for transmission and reception is referred to as a raster, and a plane defined by the oscillation movement or parallel translation of ultrasound beams is referred to as a scan plane. The transmitter/receiver controller 2 sums or amplifies received electrical signals output from transducer elements in the transducer array 1 for each raster.

An envelope detector 3 detects variations (envelope) of the signal strength along the direction of depth of a received signal associated with each raster. The detected signals are sent via a digital scan converter (DSC) 6 to a color conversion unit 8 where they are converted into brightness signals. The brightness signals are then displayed as a B-mode image on a TV monitor 9.

A spectrum Doppler signal processing unit 4, which is what is referred to as a one-point Doppler processor, samples and holds received signals output from the transmitter/receiver controller 2 at regular time intervals and detects the distribution (Doppler spectrum) of a difference (Doppler-shifted frequency) between transmitted and received frequencies for a sample volume (a specific observed region) in real time. The Doppler spectrum is fed via the digital scan converter 6 into the color conversion unit 8 and then displayed as the distribution of blood flow velocity within the sample volume on the monitor 9.

To the transmitter/receiver controller 2 is further connected a color flow mapping (CFM) unit 5, which measures Doppler shifted frequencies at a large number of points in the scanning plane and calculates the average velocity, variance and power of the blood flow from the Doppler shifted frequencies. The average velocity, variance and power are supplied, combined appropriately, to the color conversion unit 8 via the digital scan converter 6, so that they are converted to color data and then displayed as a color flow mapping image (a two-dimensional color image of the average velocity, etc.) on the monitor 9.

In FIG. 2 there is illustrated a block diagram of the color flow mapping unit 5. In order to distinguish between blood flow moving toward the transducer array 1 and blood flow moving away from the transducer array, the transmitter/receiver controller 2 outputs each received signal as it is on one hand, while introducing a 90-degree phase shift into it on the other hand, thereby providing two quadrature receive signals Re (real) and Im (imaginary). The quadrature signals are fed via a buffer memory 21 into an MTI (Moving Target Indication) filter 22 having a highpass filtering characteristic. The MTI filter 22 removes clutter components due to reflections from tissue boundaries (e.g., organ walls) and sidelobes from the quadrature signals. As a result, Doppler shifted frequencies associated with blood flow are obtained. The Doppler shifted frequencies are output via a frequency analyzer 23 and a buffer memory 24 to the digital scan converter 6 as the average velocity, variance and power of blood flow.

Figure 3:
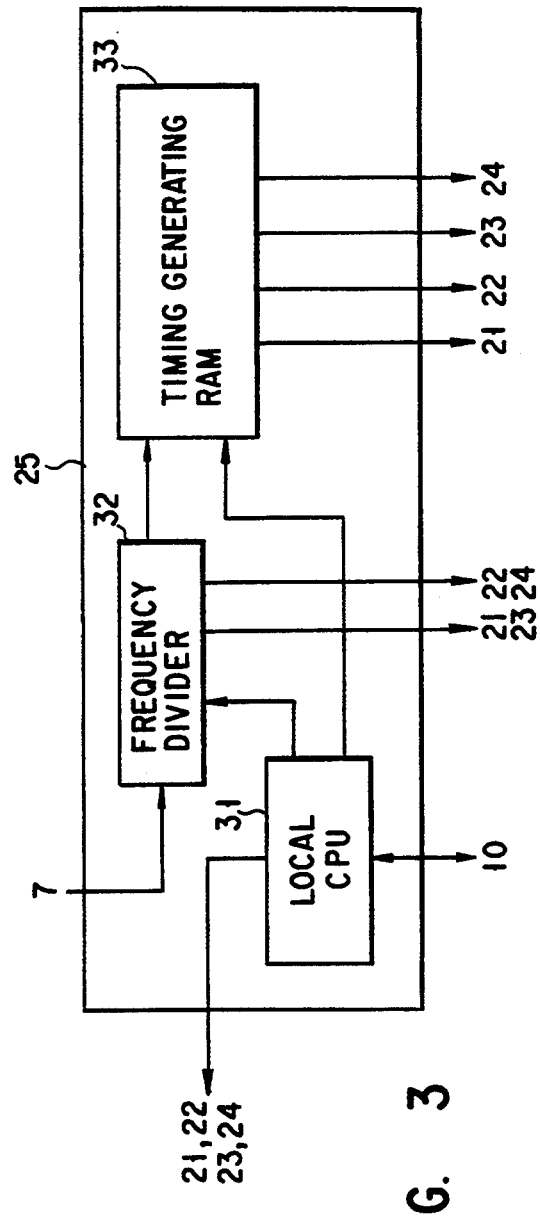
FIG. 3 is a block diagram of the unit controller of FIG. 2.

FIG. 3 is a block diagram of a unit controller 25 of FIG. 2. To the inputs of a frequency divider 32 a system timing generator 7 which sets the operating frequency of the whole system is connected directly and a main controller 10 is connected via a local CPU 31. An output signal of the frequency divider 32 is applied to a timing generating RAM 33 as an address signal. An operating frequency stored in the location designated by that address is read from the RAM 33 and sent to the buffer memory 21, the MTI filter 22, the frequency analyzer 23, and the buffer memory 24.

Figure 4:
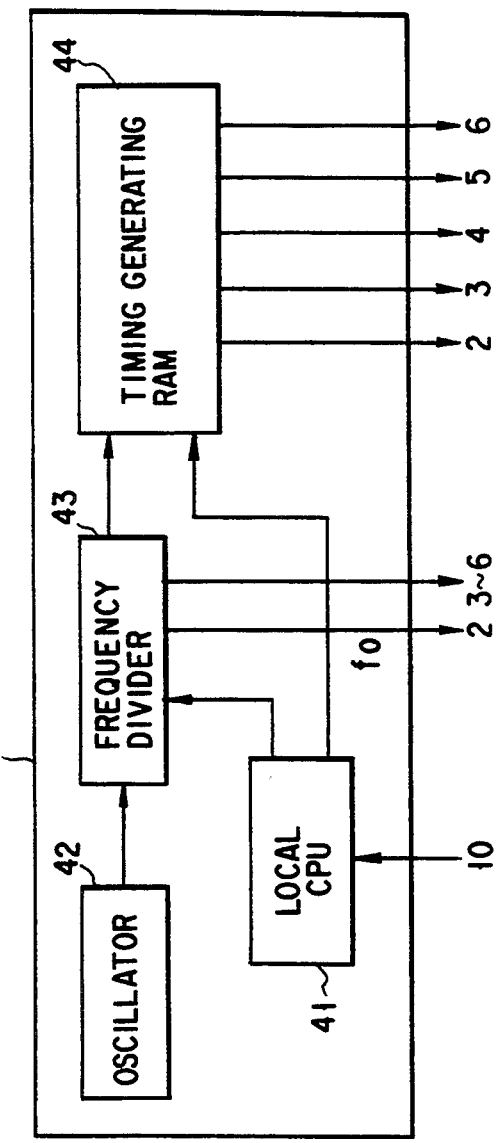
FIG. 4 is a block diagram of the system timing generator of FIG. 1.

In FIG. 4 there is illustrated in block diagram form an arrangement of the system timing generator 7. An frequency divider 43 is connected to receive an output signal of an oscillator 42 directly and a control signal from the main controller 10 via a local CPU 41. An output signal of the frequency divider 43 is fed into a timing generator RAM 44 as an address signal, so that a reference signal stored in the location designated by that address is read from the RAM and applied to the units 2, 3, 4, 5, and 6.

The main controller 10 sets a plurality of parameters required to detect data on the movement of blood flow at many points in a scanning plane, i.e., Doppler shifted frequencies, and controls the operation of the transmitter/receiver controller 2 and the color flow mapping unit 5. The parameters are as follows:

N = number of times transmission/reception is performed for the same raster (hereinafter referred to as the number of pieces of data);

fr = rate frequency to determine the repetition period of ultrasound transmission/reception;

P = low flow velocity detectability improvement ratio (also called the number of alternate stages), i.e., the number of other rasters on which ultrasound transmitting/receiving operations are performed between the moment that an ultrasound transmitting/receiving operation was performed on a certain raster and the moment that another ultrasound transmitting/receiving operation is performed on the same raster;

fc = cutoff frequency of an MTI filter, which permits discrimination between clutter components and blood flow components contained in Doppler shifted frequencies;

MA = Moving Average; the average distance (or average time) the blood flows in the direction depth MAE = Motion Artifact eliminator; the parameter required to discriminate the blood-flow component and the clutter component, by utilizing the partial or time continuity of the average speed of the blood flow the variance of this speed, and the power of the blood flower.

Figure 5:
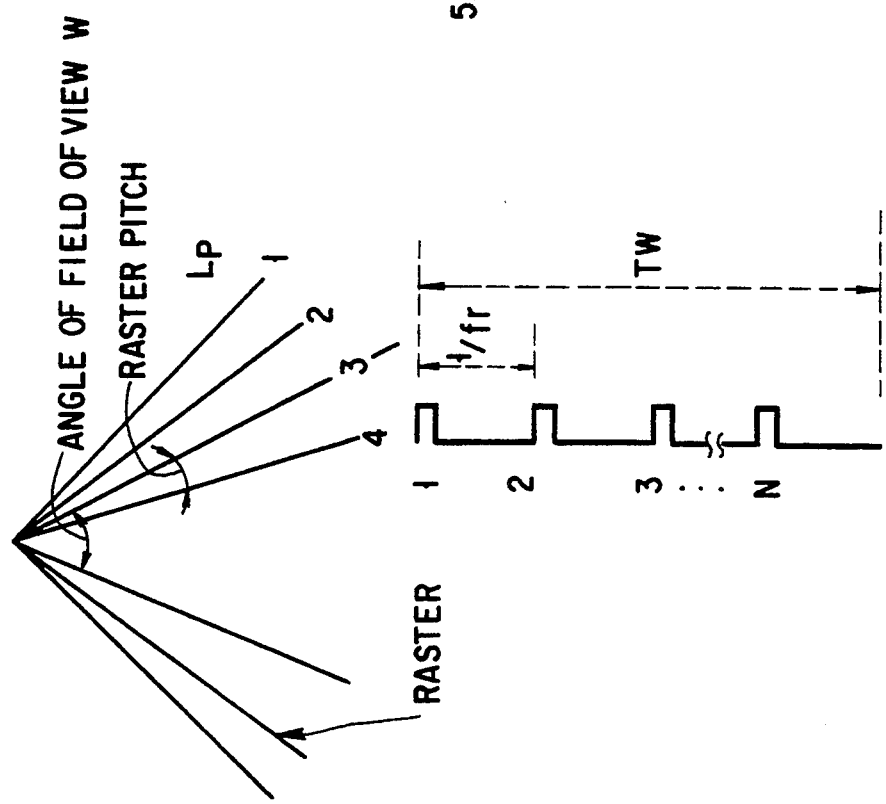
FIG. 5 is a diagram explanatory of parameters.

W = angle of field of view, i.e., the maximum sector scan angle;

Lp = raster pitch, i.e., an angle between adjacent rasters;

Ln = number of rasters in a scanning plane for some of the above parameters refer to FIG. 5.

The ultrasonic imaging apparatus (the transmitter/receiver controller 2 and the color flow mapping unit 5 in particular) needs the above-described parameters when it works in the color flow mapping mode. The parameters uniquely determine the performance of the color flow mapping mode. i.e., the detectable minimum velocity Vmin, the detectable maximum velocity Vmax, and the frame rate FR (f/s). It is this performance of the color flow mapping mode that an operator wants to know ultimately. The blood flow velocity differs among imaging regions such as circulatory system, peripheral vasculature (PV), and pars abdominal system. It is therefore required to change the detectable minimum velocity Vmin, the detectable maximum velocity Vmax, and the frame rate FR (f/s) from imaging region to imaging region. Even with the same imaging region, however, there is a difference in blood flow velocity among individuals. Also there is a difference in quantity and velocity of abnormal blood flow (reverse flow) among delicate positions within an imaging region. It will therefore be impossible to keep unchanged the detectable minimum velocity Vmin, the detectable maximum velocity Vmax, and the frame rate FR (f/s) even for the same imaging region of a subject under examination.

In a memory 12 connected to the main controller 10 there are stored a plurality of patterns for each of different types of imaging regions, such as circulatory system, peripheral vasculature (pv), pars abdominal system, etc., each pattern including appropriately adjusted values of preset values of the detectable minimum velocity Vmin, the detectable maximum velocity Vmax, and the frame rate FR (f/s). That is, when an image region is specified, a plurality of patterns corresponding to this imaging region are read out from that memory. When a certain pattern is specified, the values of the above-described parameters are calculated by the main controller 10 so as to satisfy the following equations.

$$Vmin = \alpha \times ((C \times fr)/(2 \times N \times P \times f0 \times \cos \theta)) \quad (7)$$

$$Vmax = \alpha \times ((C \times fr)/(4 \times P \times f0 \times \cos \theta)) \quad (8)$$

where $\alpha$ is a constant.

$$f/s = \beta \times (fr/(Ln \times N)) \quad (9)$$

where $\beta$ is a constant.

$$Ln = \gamma \times (W/LP) \quad (10)$$

where $\gamma$ is a constant.

Of course, the values of these parameters may be calculated in advance for each pattern and stored in the memory 12.

Figure 6:
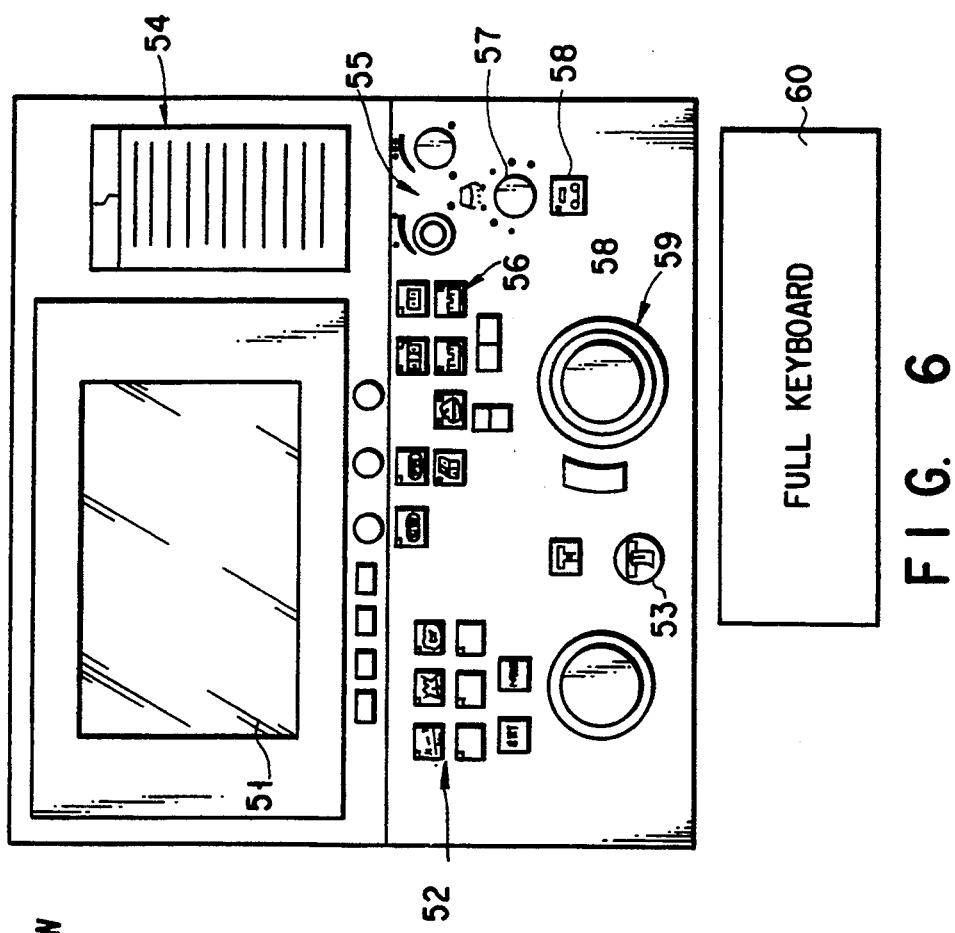
FIG. 6 is an exterior view of the operating panel of FIG. 1.

To the main controller 10 is connected an operating panel 11, which is quipped, as shown in FIG. 6, with a touch screen 51, a full keyboard 60, and various switches. The switches include a rotary switch 59 for making a selection among patterns, a switch 52 for making a selection among body marks, a control switch 53 for an external printer, an STC (Sensitive Time Control) switch 54, a gain control switch 55, a mode selection switch 56 for making a selection among B mode, one-point mode and color flow mapping mode, a switch 57 for making a selection among depths of field of view, and an external VTR control switch. The full keyboard is used to enter patient attributes such as names.

Figure 7:
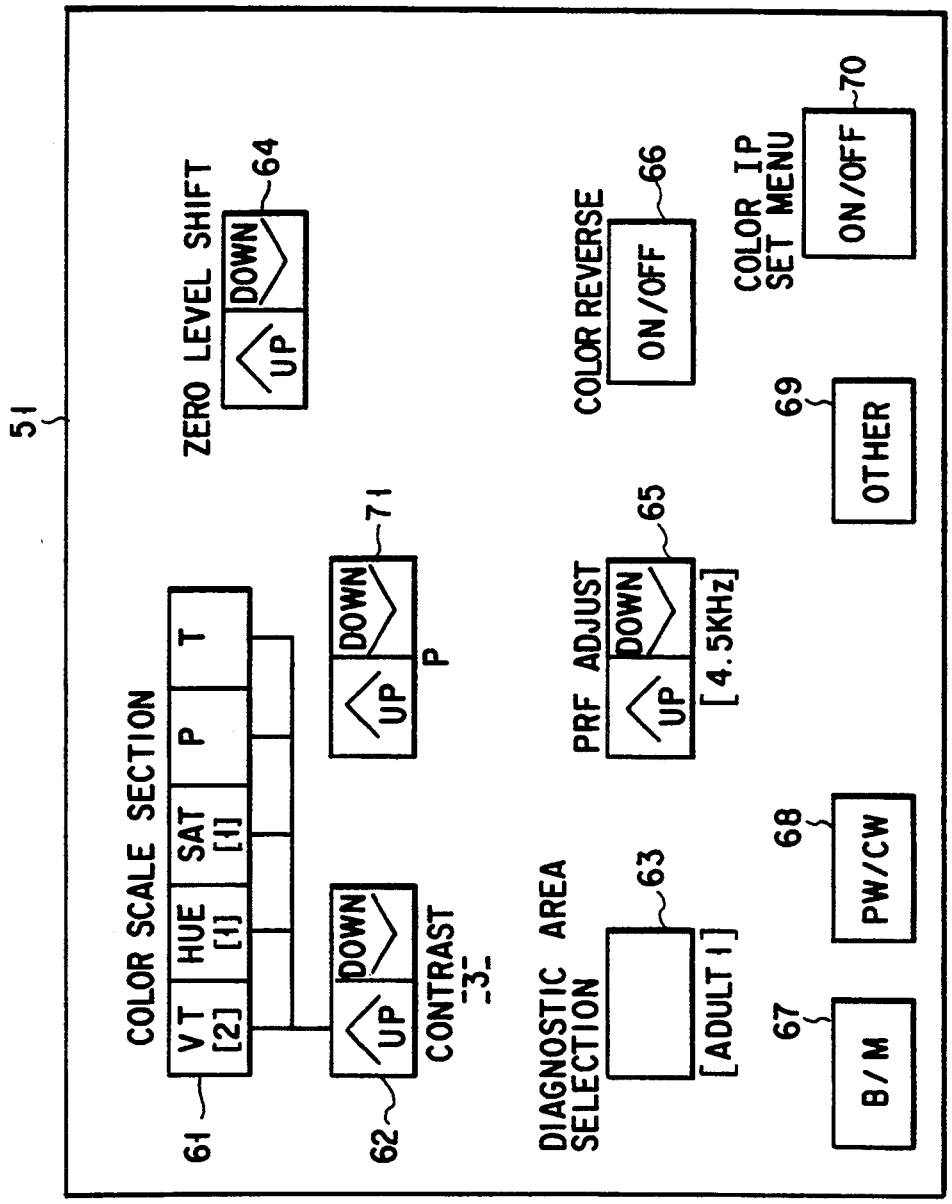
FIG. 7 illustrates a display menu displayed on the touch screen of FIG. 6.

In FIG. 7 there is shown a display menu, which is displayed on the touch screen 51 when the color flow mapping mode is selected by the mode selection switch 56. The display menu includes a touch switch 63 for making a selection among regions to be imaged for diagnosis, a touch switch 61 for making a selection among color scales, a touch switch 62 for adjusting contrast, a touch switch for adjusting zero level shift, a touch switch 65 for adjusting the rate frequency, a touch switch 66 for changing the correspondence between blood flow direction (forward, reverse) and color (red, blue), touch switches 67 and 68 for activating the B mode and the one-point Doppler mode in addition to the color flow mapping mode, a touch switch 69 for changing the menu to a display menu for changing the above-described parameters forcibly, and a touch switch 70 for changing to a display menu for changing the parameters.

Figure 8:
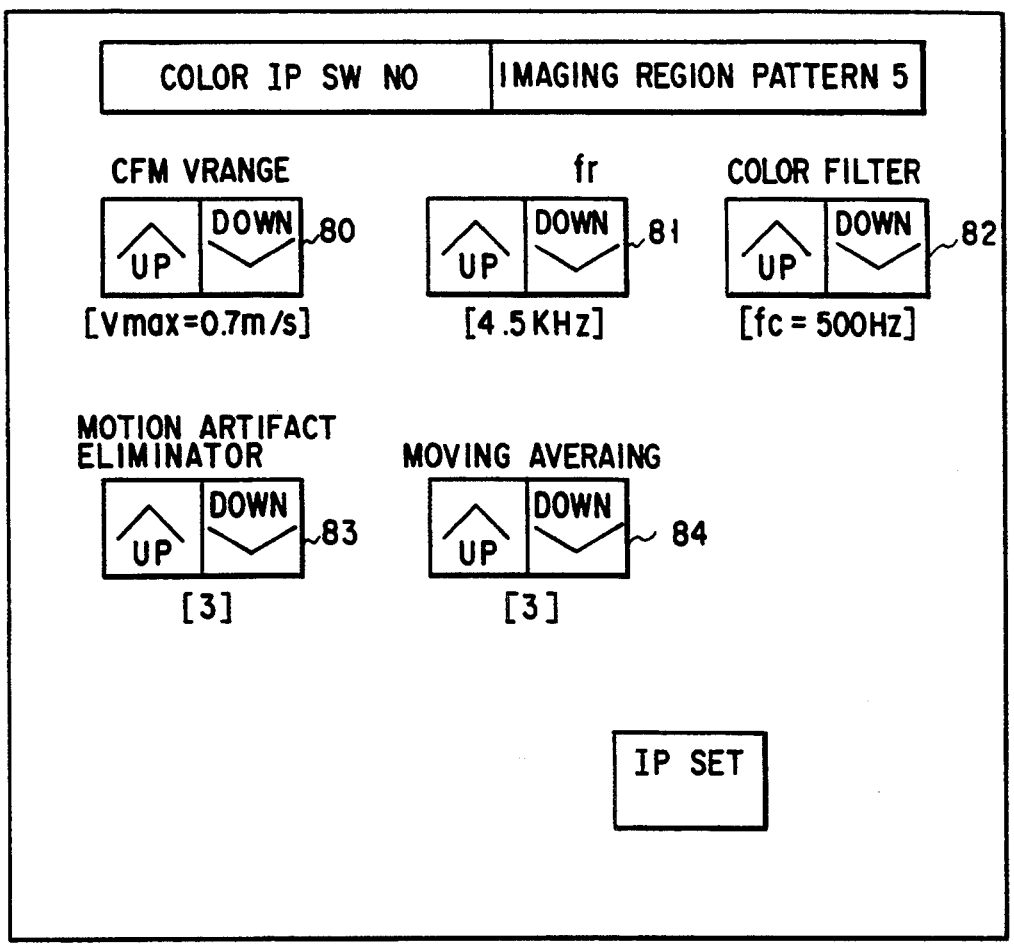
FIG. 8 illustrates the lower menu of the display menu of FIG. 7.

When the touch switch 70 is specified, the display menu shown in FIG. 7 is switched to such a pattern changing display menu as shown in FIG. 8. This display menu includes a touch switch 80 for adjusting the number of alternate stages P (CFM VRANGE) forcibly, a touch switch 81 for adjusting the rate frequency fr forcibly, a touch switch 82 for adjusting the cutoff frequency of the MTI filter forcibly, a touch switch 83 for adjusting the MAE (Motion Artifact eliminator) forcibly, a touch switch 84 for adjusting the MA (Moving Average), and several switches (not shown) for adjusting other parameters forcibly.

Figure 9A:
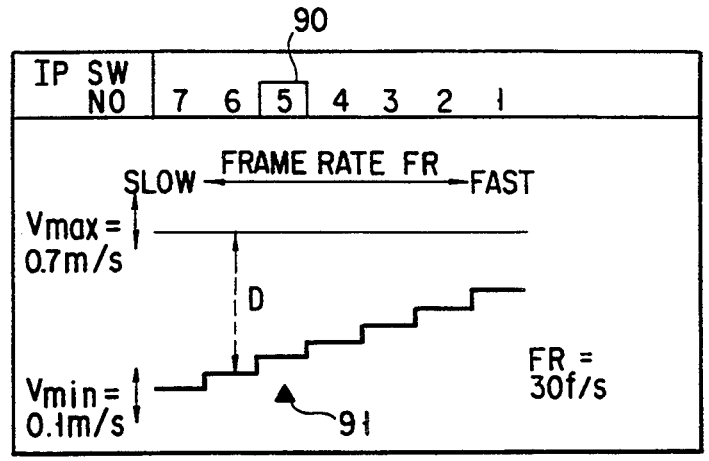
FIGS. 9A, 9B and 9C illustrates a plurality of patterns for different imaging regions which are simultaneously displayed on the display screen.
Figure 9B:
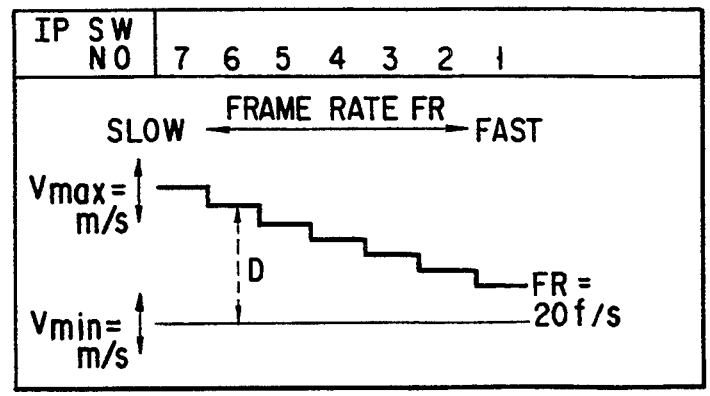
Figure 9C:
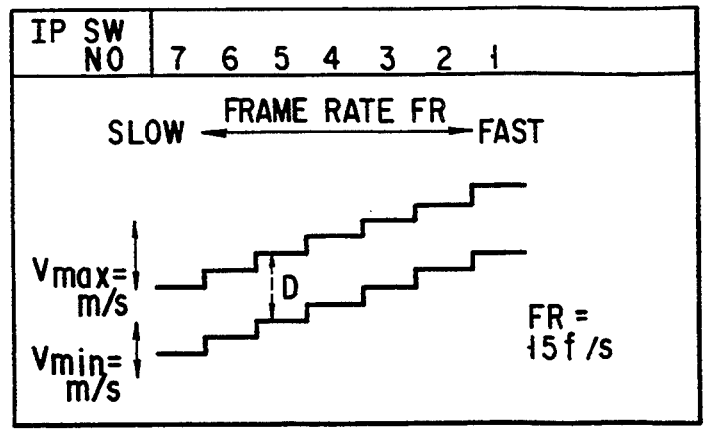

When the color flow mapping mode is selected by the mode selection switch 56 and a body region to be imaged is selected by the touch switch 63, a plurality of patterns (the number of which is assumed herein to be seven) for that body region are read from the memory 12 into the main controller 10. The main controller 10 then organizes the seven patterns into an image and outputs it to the color conversion unit 8. Thus, the seven patterns are displayed simultaneously on the screen of the TV monitor 9 as shown in FIG. 9A, FIG. 9B, or FIG. 9C. More specifically. FIG. 9A shows the seven patterns corresponding to a circulatory organ system, FIG. 9B shows the seven patterns corresponding to peripheral vasculature (PV), and FIG. 9C shows the seven patterns for the pars abdominal system. On the pattern display screen, the detectable minimum velocity Vmin and the detectable maximum velocity Vmax are numerically displayed in units of m/s, the number of frames per second f/s is numerically displayed, the frame rates FR for the respective patterns are displayed relatively (slow–fast), and variations in the detectable minimum velocity Vmin and the detectable maximum velocity Vmax between successive patterns are displayed graphically. D represents a difference between the minimum velocity Vmin and the maximum velocity Vmax, i.e., a detectable range of velocity. With the circulatory organ system shown in FIG. 9A, the seven patterns are selected such that the reflected level is made constant by keeping the maximum velocity fixed, and the frame rate FR (the number of frames) increases with increasing minimum velocity Vmin. With peripheral vasculature (Pv) shown in FIG. 9B, the seven patterns are selected such that the minimum velocity Vmin is kept fixed, and the frame rate FR (the number of frames) increases with decreasing maximum velocity Vmax. In the pars abdominal system shown in FIG. 9C, the seven patterns are selected such that the frame rate FR (the number of frames) is kept fixed, and the maximum velocity Vmax and the minimum velocity Vmin vary interlocked with each other.

Of the seven patterns thus displayed simultaneously, a pattern is selected by operating the pattern selecting rotary switch 59. For example, cursors 90 and 91 move as the rotary switch 59 is operated step by step.

When a pattern is selected, the values of parameters for implementing this pattern are calculated by the main controller 10. Or, if parameter values for each of all patterns have been stored in the memory 12, then the parameter values for that pattern selected will be read from the memory 12 into the main controller 10. The main controller 10 controls the transmitter/receiver controller 2 and the color flow mapping unit 5 in accordance with the parameter values thus obtained, effecting the color flow mapping for that pattern.

Thus, the maximum velocity Vmax, the minimum velocity Vmin, and the frame rate FR (the number of frames) for several patterns are provided from the apparatus side. To determine the maximum velocity Vmax, the minimum velocity Vmin and the frame rate FR (the number of frames), the values of parameters, such as the number of pieces of data N, the rate frequency fr, the number of alternate stages P, the cutoff frequency fc, the Moving Average MA, the Motion Artifact eliminator MAE, the angle of field of view, the raster pitch LP, and the number of rasters Ln, are set on the apparatus side.

Therefore, the operator is relieved of the burden of setting each of such parameters individually. Moreover, the operator is relieved of the burden of calculating the maximum velocity Vmax, the minimum velocity Vmin and the frame rate (the number of frames) that the operator wants to know truly from the set values of parameters. Furthermore, there is no need of correcting parameters which have been set to values impossible to implement by mistake, over and over again.

A plurality of patterns can be narrowed down to a relatively small number of patterns by making a selection among regions to be image or diagnosed. Moreover, a relatively small number of patterns for a region selected are displayed simultaneously. Furthermore, the maximum velocity Vmax, the minimum velocity Vmin and the number of frames f/s are displayed in terms of numerical values. Therefore, the operator, being given sufficient factors in decision, is allowed to select a desired pattern readily.

Figure 10A:
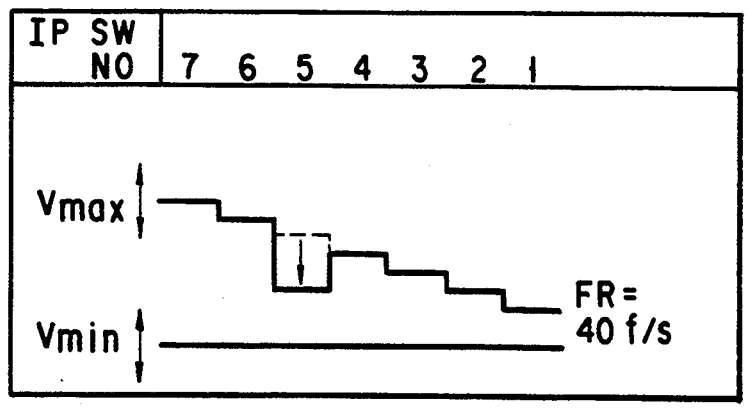
FIGS. 10A and 10B illustrate certain patterns subjected to variations.
Figure 10B:
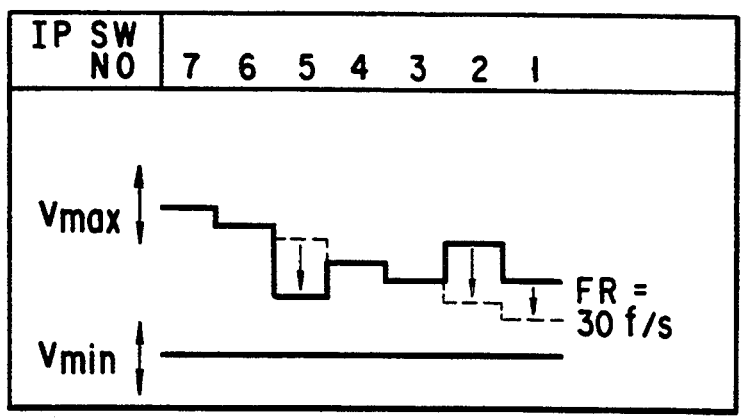

The operator is allowed to change each of the maximum velocity Vmax, the minimum velocity Vmin, and the frame rate FR (the number of frames) associated with a desired pattern. First, the operator operates the touch switch 70 with the result that the display menu shown in FIG. 8 is displayed for changing the pattern forcibly. The operator next operates the touch switch 80 for adjusting the number of alternate stages P (CFW VRANGE) forcibly, the touch switch 81 for adjusting the rate frequency fc forcibly, the touch switch 82 for adjusting the cutoff frequency fc of the MTI filter forcibly, the touch switch 83 for adjusting the MAE (Motion Artifact eliminator) forcibly, the touch switch 84 for adjusting the MA (Moving Average) forcibly, and one or more switches of other touch switches for adjusting other parameters forcibly. At this point, one or more unchanged parameters may be changed in the main controller 10 so as to effect the color flow mapping. The main controller 10 uses the one or more parameters already changed to calculate the maximum velocity Vmax, the minimum velocity Vmin, and the frame rate FR (the number of frames) associated with a selected pattern in accordance with equations (7), (8), (9) and (10). As shown in FIGS. 10A and 10B, the displayed patterns reflect the results of these calculations. It should be noted here that the maximum velocity Vmax, the minimum velocity Vmin and the frame rate FR (the number of frames) of a desired pattern may be changed directly on the display screen as shown in FIG. 9A, 9B or 9C without changing parameters with the touch switches for the respective parameters on the display menu shown in FIG. 8. In this case, the main controller 10 would calculate the parameters so as to permit the color flow mapping on the basis of the changed pattern.

Although the preferred embodiment of the present invention has been disclosed or described, it is apparent that other embodiments and modifications are possible.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic imaging apparatus comprising:
    an ultrasonic transducer array for transmitting ultrasonic waves to a subject under examination and receiving ultrasonic waves reflected from within said subject under examination;
    scan control means for controlling said transducer array so as to transmit/receive said ultrasonic waves in the same direction repeatedly and change the transmitting/receiving direction of said ultrasonic waves in a sectional plane of said subject under examination;
    detecting means for detecting Doppler shifted frequency data at a plurality of points in said sectional plane from a received signal by said transducer array;
    displaying means responsive to said Doppler shifted frequency data for displaying blood flow of the subject in said sectional plane in color;
    storage means for storing a plurality of types of patterns having a maximum velocity, a minimum velocity and a number of frames per unit time of blood flow to be detected by said detecting means in various combinations;
    selecting means for selecting a pattern out of said plurality of types of patterns manually; and
    control means for setting a parameter for the number of times said ultrasonic waves are transmitted/received repeatedly in the same direction, a parameter for a repetition period at which said ultrasonic waves are transmitted/received repeatedly, and a parameter for the number of times the direction of transmission/reception of said ultrasonic waves is changed in said scanning plane and controlling said scan control means and said detecting means in accordance with said parameters thus set so as to implement said pattern selected by said selecting means.

2. The ultrasonic imaging apparatus according to claim 1, further comprising specifying means for specifying an imaging region out of a plurality of types of imaging regions manually.

3. The ultrasonic imaging apparatus according to claim 2, in which said storage means stores a plurality of types of patterns for each of said plurality of types of imaging regions, a plurality of types of patterns being read out when an image region is specified by said specifying means, and in which said selecting means includes display means for displaying said plurality of types of patterns read out of said storage means simultaneously on its display screen.

4. The ultrasonic imaging apparatus according to claim 3, in which said display means displays the minimum velocity, the maximum velocity and the number of frames per unit time associated with each of said plurality of types of patterns numerically and displays variations in minimum velocity and maximum velocity between successive patterns graphically.

5. The ultrasonic imaging apparatus according to claim 3, in which, in said plurality of types of patterns for an imaging region of said plurality of types of imaging regions, the maximum velocity is kept fixed, the minimum velocity is changed, and the number of frames per unit time is changed in reverse proportion to the minimum velocity.

6. The ultrasonic imaging apparatus according to claim 3, in which, in said plurality of types of patterns for an imaging region of said plurality of types of imaging regions, the minimum velocity is kept fixed, the maximum velocity is changed, and the number of frames per unit time is changed in reverse proportion to the minimum velocity.

7. The ultrasonic imaging apparatus according to claim 3, in which in said plurality of types of patterns for an imaging region of said plurality of types of imaging regions, the number of frames per unit time is kept fixed, and the maximum velocity and the minimum velocity are changed interlocked with each other.

8. The ultrasonic imaging apparatus according to claim 1, in which said storage means stores said parameters which have been calculated in advance for each of said plurality types of patterns, and in which said control means reads parameters for a pattern selected by said selecting means from said storage means.

9. The ultrasonic imaging apparatus according to claim 1, in which said control means calculates parameters to implement a pattern selected by said selecting means.

10. The ultrasonic imaging apparatus according to claim 1, in which said control means further sets a parameter for the number of times ultrasonic waves are transmitted/received in other directions during a time interval between the moment that ultrasonic waves are transmitted/received in one direction in said sectional plane and the moment that ultrasonic waves are transmitted/received again in the same direction.

11. The ultrasonic imaging apparatus according to claim 1, in which said control means further sets a parameter for the range of said sectional plane and a parameter for a pitch at which the direction in which ultrasonic waves are transmitted is changed.

12. The ultrasonic imaging apparatus according to claim 1, in which said detecting means includes a filter means for removing clutter components from said Doppler shifted frequency data, and in which said control means further sets a parameter for the cutoff frequency of said filter means.

13. The ultrasonic imaging apparatus according to claim 1, in which said control means further sets a parameter for moving average.

14. The ultrasonic imaging apparatus according to claim 1, in which said control means further sets a parameter for a motion artifact eliminator.

15. The ultrasonic imaging apparatus according to claim 1, further comprising manual changing means for manually changing said parameter for the number of times ultrasonic waves are transmitted repeatedly in the same direction forcibly, manual changing means for manually changing said parameter for a repetition period at which ultrasonic waves are transmitted repeatedly in the same direction forcibly, and manual changing means for manually changing said parameter for the number of times the direction of transmission of ultrasonic waves is changed in said scanning plane forcibly.

16. The ultrasonic imaging apparatus according to claim 15, in which said control means is responsive to the results of changes made by said manual changing means to update said parameter for the number of times ultrasonic waves are transmitted repeatedly in the same direction, said parameter for a repetition period at which ultrasonic waves are transmitted repeatedly in the same direction, and said parameter for the number of times the direction of transmission of ultrasonic waves is changed in said scanning plane.

17. The ultrasonic imaging apparatus according to claim 16, in which said control means stores updated parameters in said storage means.

* * * * *